US008269830B1

(12) United States Patent
Delaney

(10) Patent No.: US 8,269,830 B1
(45) Date of Patent: Sep. 18, 2012

(54) INSPECTING POTENTIALLY INTERFERING FEATURES IN A MACHINE VISION SYSTEM

(75) Inventor: Mark Lawrence Delaney, Shoreline, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 15 days.

(21) Appl. No.: 13/086,912

(22) Filed: Apr. 14, 2011

(51) Int. Cl.
*H04N 7/18* (2006.01)

(52) U.S. Cl. .......................... 348/87; 348/126
(58) Field of Classification Search .............. 348/86–95, 348/125–141
See application file for complete search history.

(56) References Cited

U.S. PATENT DOCUMENTS

| 7,324,682 | B2 | 1/2008 | Wasserman |
| 7,454,053 | B2 | 11/2008 | Bryll |
| 7,522,763 | B2 | 4/2009 | Tessadro |
| 7,583,852 | B2 | 9/2009 | Venkatachalam |
| 7,627,162 | B2 | 12/2009 | Blanford |
| 7,656,425 | B2 * | 2/2010 | Tobiason et al. .............. 348/187 |
| 7,769,222 | B2 | 8/2010 | Blanford, Jr. |
| 2010/0158343 | A1 | 6/2010 | Bryll |

OTHER PUBLICATIONS

Campbell, S.R., "Autofocus Video Tool and Method for Precise Dimensional Inspection," U.S. Appl. No. 12/608,943, filed Oct. 29, 2009.

Delaney, M.L., "Precision Solder Resist Registration Inspection Method," U.S. Appl. No. 12/904,013, filed Oct. 13, 2010.
"QVPAK 3D CNC Vision Measuring Machine: Operation Guide," Version 2.0, Manual No. 4911GB, Series No. 359, Mitutoyo Corporation & Micro Encoder Inc., Kanagawa, Japan, Sep. 1996, 86 pages.
"QVPAK 3D CNC Vision Measuring Machine: User's Guide," Version 7.1, 2d ed., Manual No. 99MCB225A, Series No. 359, Mitutoyo Corporation & Micro Encoder Inc., Kanagawa, Japan, Sep. 2003, 370 pages.

* cited by examiner

*Primary Examiner* — Andy Rao
(74) *Attorney, Agent, or Firm* — Christensen O'Connor Johnson Kindness PLLC

(57) ABSTRACT

A robust video tool is provided for use in a machine vision inspection system. The robust video tool comprises a region of interest, a user interface, edge detection operations, and excluded region operations that determine a set of current-feature edge points which includes edge points detected in the region of interest and excludes edge points in an excluded region. The excluded region is determined by an excluded region generator, based on at least one previously characterized feature which is a feature characterized by using a video tool that detects the edge points of, and characterizes dimensional parameters of, the previously characterized feature. Importantly, the robust video tool features and operations are configured to allow learn mode programming on a workpiece that is either properly fabricated or improperly fabricated, and the resulting program will operate reliably on a run mode workpiece that is either properly fabricated or improperly fabricated.

20 Claims, 5 Drawing Sheets

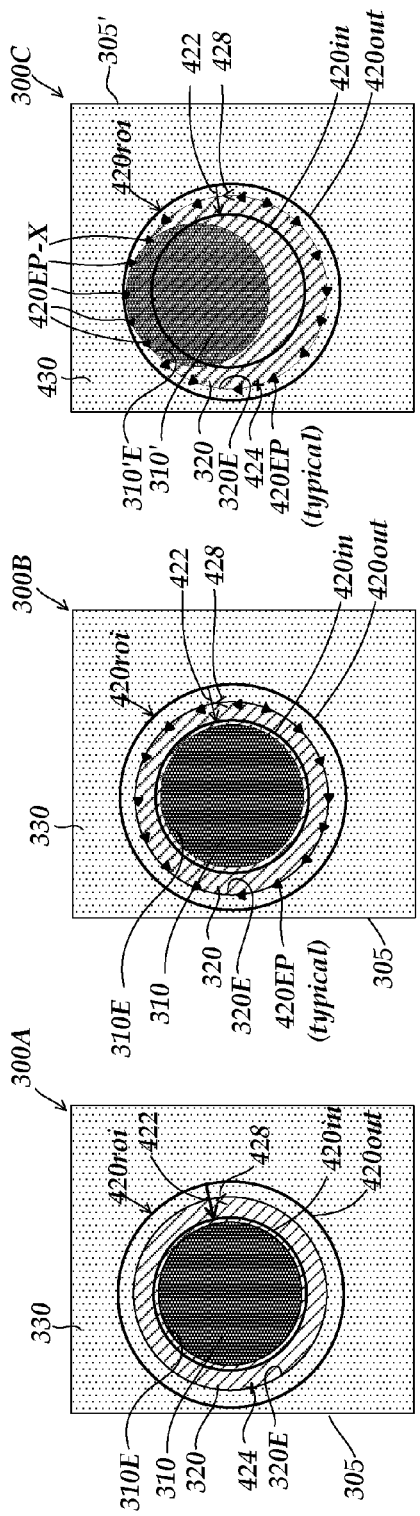
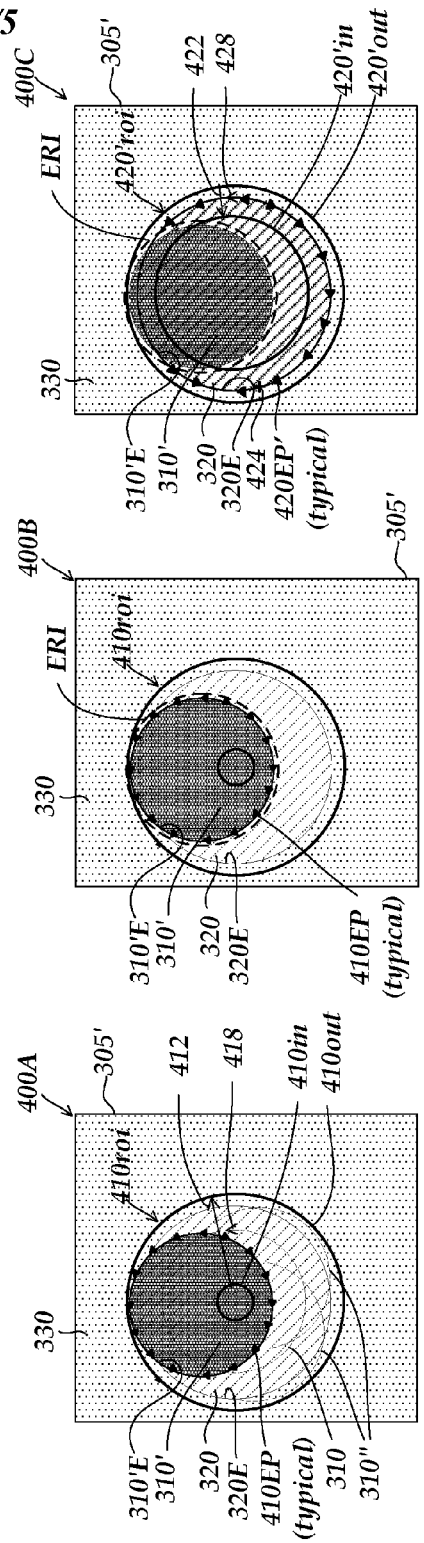

INSPECTING POTENTIALLY INTERFERING FEATURES IN A MACHINE VISION SYSTEM

FIELD OF THE INVENTION

The invention relates generally to machine vision inspection systems, and more particularly to methods of inspecting potentially interfering features on a workpiece.

BACKGROUND OF THE INVENTION

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 (the '180 patent) teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs." Video tools may include, for example, edge/boundary detection tools, autofocus tools, shape or pattern matching tools, dimension measuring tools, and the like.

One application for a machine vision inspection system is the inspection of features on a workpiece. In some cases, these features may be contained in different layers and/or may interfere or have overlapping edges. One example of such a workpiece is a printed circuit board (PCB), wherein it may be desirable to measure the registration relationship between a pattern in a solder resist layer and conductive features intended to be exposed and/or insulated by the solder resist layer. Such features may be concentric, or in some cases, fabrication errors may occur which cause the edges of some of the features to overlap or interfere. Such errors may be associated with short circuiting or other problems for the operation of the PCB. Thus, during the inspection of the PCB, it is important to be able to accurately determine if the features are properly located. However, prior art methods for automatically inspecting such features are neither easy enough to program for unskilled users of the machine vision inspection system, nor robust enough to operate properly under a wide variety of possible alignments and misalignment conditions for the related features, which may potentially not overlap, or overlap to various degrees. Improvements in programming and techniques related to accurately detecting and/or measuring potentially overlapping or interfering features on workpieces such as PCBs, would be desirable.

SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A machine vision inspection system includes features for programming and techniques related to inspecting potentially interfering features on a workpiece. The machine vision inspection system may comprise: a control system comprising a memory element and an excluded region generator; an imaging system operable to provide workpiece images; a display usable to display workpiece images and user interface elements; a user interface usable to define a sequence of workpiece inspection operations including video tool operations which analyze workpiece images, detect edge points of a workpiece feature, and characterize at least the location of the workpiece feature, and a plurality of video tools including a robust video tool that performs edge detection. The robust video tool comprises a region of interest, a robust video tool interface included in the user interface, operations that detect edge points in the region of interest, and excluded region operations that analyze a workpiece image and determine a set of current-feature edge points such that the set of current-feature edge points includes edge points detected in the region of interest and does not include edge points located within an excluded region that is determined based on at least one previously characterized feature. A previously characterized feature, as disclosed herein, is defined to be a feature characterized by using one of the plurality of video tools of the machine vision inspection system to analyze a workpiece image to detect edge points of the previously characterized feature and characterize a dimensional parameter of the previously characterized feature based on the detected edge points. According to the principles of this invention, the excluded region generator is configured to determine the excluded region based on at least one previously characterized feature.

It should be appreciated that the term "previously characterized feature" is sometimes used herein as a descriptive name for a workpiece feature which is eventually used in the capacity of a "previously characterized feature" for the purposes of determining an excluded region, even when referring to that workpiece feature before it has actually been characterized. Similarly, the term "current feature" is sometimes used herein as a descriptive name for a workpiece feature which may be subject to interference from the "previously characterized feature" when it is eventually analyzed (e.g., using a robust video tool as disclosed herein), even when referring to that workpiece feature at a time before or after it is actually analyzed.

In some embodiments, the excluded region generator is configured to determine the excluded region based on a set of excluded region parameters defined during learn mode, the set of excluded region parameters including an identification of the at least one previously characterized feature that is used to determine the excluded region. In some embodiments, the excluded region generator may be configured to automatically identify a previously characterized feature that is closest to a current instance of the robust video tool during learn mode, and automatically include an identification of that previously characterized feature in the set of excluded region parameters that is used to determine the excluded region.

In some embodiments, the user interface is configured to define the parameters of at least one instance of a video tool in order to provide a characterization of the at least one previously characterized feature using a representative workpiece during learn mode, and the robust video tool interface is configured to define the parameters of a current instance of the robust video tool which is used to determine a set of current-feature edge points for a current feature on the representative workpiece during learn mode, and the machine vision inspection system is configured to record those parameters and the defined set of excluded region parameters in a part program. The machine vision inspection system may be configured to execute operations of the part program during the run mode of operation for a run mode workpiece similar to the representative workpiece. Those operations may comprise using the recorded defined parameters to provide the characterization of the at least one previously characterized feature on the run mode workpiece, that is, to characterize the at least one feature on the run mode workpiece that corresponds to the at least one previously characterized feature on the similar representative learn mode workpiece. Those operations may further comprise using the recorded excluded region parameters to determine the excluded region based on the at least one previously characterized feature on the run mode workpiece, and using the recorded defined parameters of the current instance of the robust video tool to determine a set of current-feature edge points for the current feature on the run mode workpiece, such that the set of current-feature edge points includes edge points detected in the region of interest of the current instance of the robust video tool on the run mode workpiece and does not include edge points located within the excluded region that is determined based on the at least one previously characterized feature on the run mode workpiece.

In various embodiments the user interface is configured such that a user can select and configure the at least one instance of a video tool included in the plurality of video tools, wherein that video tool is one of a circle tool having an annular region of interest, an arc tool having an arc-shaped region of interest, and a tool that characterizes a straight edge and has a rectangular region of interest; and a user interface of that video tool includes a region of interest indicator which is superimposed on the displayed image of the representative workpiece during learn mode. The user interface of that video tool is configured by the user in order to define the parameters of an instance of that video tool in order to provide the at least one previously characterized feature using the representative workpiece during the learn mode of operation. In various embodiments, the user interface is configured such that a user can select and configure an instance of the robust video tool, wherein the robust video tool is also one of a circle tool having an annular region of interest, an arc tool having an arc-shaped region of interest, and a tool that characterizes a straight edge and has a rectangular region of interest; and the robust video tool interface includes a region of interest indicator and an excluded region indicator which are superimposed on a displayed image of the representative workpiece during learn mode. The robust video tool interface is configured by the user in order to define the parameters of the current instance of the robust video tool used to determine the set of current-feature edge points for a current feature on the representative workpiece during the learn mode of operation.

In some embodiments, the user interface comprises an excluded region parameter portion which is configured to define members of the set of excluded region parameters during the learn mode of operation of the machine vision inspection system, and the defined members include an identification of the at least one previously characterized feature used to determine the excluded region. The excluded region parameter portion may comprise an excluded feature identifier that is configured by the user to provide the identification of the at least one previously characterized feature that is used to determine the excluded region. In some embodiments, the excluded region parameter portion comprises a list of previously characterized features that is automatically generated by the control system and the excluded feature identifier comprises a selection element that is configured to select at least one member of the list to include in the identification of the at least one previously characterized feature that is used to determine the excluded region.

In some embodiments, the excluded region parameter portion is included in the robust video tool interface, and the robust video tool interface is configured to define the parameters of a current instance of the robust video tool during learn mode, including defining a current instance of the set of excluded region parameters for an excluded region corresponding specifically to the current instance of the robust video tool. In such a case, the current instance of the set of excluded region parameters includes an identification of a current instance of the at least one previously characterized feature that is used to determine the excluded region. In some such embodiments, the robust video tool interface comprises a region of interest indicator and an excluded region indicator which are displayed superimposed on an image of the representative workpiece during the learn mode of operation. The region of interest indicator may automatically change when the current instance of the set of excluded region parameters is changed. In some embodiments, the excluded region indicator is configured to be altered by a user to adjust the size of the excluded region indicator and make a corresponding change in the current instance of the set of excluded region parameters.

In some embodiments, the excluded region generator may be configured to determine the excluded region such that it encompasses at least a majority of the edge points detected while characterizing the at least one previously characterized feature that is used to determine the excluded region. In various embodiments it is preferred that the excluded region encompass all such edge points (although, in some such cases, "outliers" in the detected edge points may fall outside of the excluded region).

In some embodiments, a previously characterized feature may be defined as a feature characterized by using one of the plurality of video tools to perform operations comprising (a) analyzing a workpiece image to detect edge points of that feature and (b) fitting a geometric feature to the detected edge points, and (c) providing a characterization of the fitted geometric feature, that characterization comprising at least a dimensional parameter of the fitted geometric feature (e.g., the video tool may be a known circle tool, or arc tool, or a tool that fits a line to a straight edge, or the like) and the excluded region generator may be configured to determine the excluded region based on the characterization of the fitted geometric feature of at least one previously characterized feature. Since such video tools exist in known machine vision inspection systems, and there are known methods for such fitted geometric features to be recorded in memory in such systems, such embodiments of the invention may be implemented with relatively little modification of existing systems and require relatively little additional training for users in order obtain the benefits of the invention.

In some embodiments, the excluded region generator is configured to determine the excluded region by adjusting at least one of the size and the location of the fitted geometric feature and using that adjusted fitted geometric feature as a boundary of the excluded region, wherein the adjusted fitted geometric feature provides a boundary that encompasses at least a majority of the detected edge points used for fitting the geometric feature. The robust video tool may comprise a scan direction that is used in its operations that detects edge points in its region of interest, and the excluded region generator may be configured to adjust the fitted geometric feature such that the boundary moves in a direction opposite to that scan direction. Moving the boundary in this direction tends to prevent the robust video tool from including edge points of the at least one previously characterized feature in the set of current-feature edge points, and the direction may be automatically chosen, in some embodiments.

The foregoing features are particularly useful for inspecting potentially overlapping circular features (e.g., holes, copper pads, and solder resist openings) on PCBs. In such applications, the previously characterized feature is a feature characterized by using a circle tool included in the plurality of video tools, the fitted geometric feature is a circle, and the robust video tool is a circle tool. Both fluorescent and non-fluorescent imaging may be useful for inspecting features on PCBs, since the PCB may include a translucent fluorescent solder resist coating, and the different types of imaging may reveal different types of features of the solder resist, and/or elements that it covers, more clearly. For example, different types of images may be provided as disclosed in copending and commonly assigned U.S. patent application Ser. No. 12/904,013, which is hereby incorporated by reference in its entirety. More generally, in some embodiments, the excluded region generator is configured to determine the excluded region based on at least one previously characterized feature that is a feature characterized in a first workpiece image that is exposed using a first set of wavelengths, and the robust video tool is configured to detect the set of current-feature edge points in a second workpiece image that is exposed using a second set of wavelengths that is different than the first set of wavelengths. In some embodiments, one of the first and second sets of wavelengths includes a fluorescent wavelength emitted by the workpiece with a significant intensity, and the other of the first and second sets of wavelengths does not include the fluorescent wavelength emitted by the workpiece with a significant intensity.

In some embodiments, the robust video tool comprises an excluded region mode wherein the excluded region operations are performed, and a non-excluded region mode comprising non-excluded region operations that analyze a workpiece image and determine a set of current-feature edge points such that the set of current-feature edge points includes edge points detected in the region of interest without consideration of an excluded region. In such cases, the robust video tool interface may include an excluded region activation element which is operable by a user to determine whether or not an instance of the robust video tool operates in the excluded region mode or the non-excluded region mode. Such a versatile robust video tool simplifies training and programming for users.

It will be appreciated that the features outlined above and disclosed in greater detail below may be particularly useful for certain applications. For example, in an implementation where the workpiece is a multiple layer workpiece (e.g., a printed circuit board including a solder resist layer), edge features in the various layers may overlap, causing conventional edge detection tools to fail or mislead due to "confusion" regarding which edge feature is in which layer and the inability to separate their respective edges. Conventional video tools have regions of interest that are unable to solve this problem, due to the fact that the features may truly overlap on some workpieces and not on others, such that the regions of interest cannot be programmed to reliably isolate a particular feature and operate effectively or reliably for all workpiece conditions. Similarly, known feature "masking" programming methods (e.g., see U.S. Pat. No. 7,324,682, which is hereby incorporated by reference in its entirety) are taught by assuming that an occluding or interfering feature is always present, and so may not operate effectively or reliably for all workpiece conditions. It should be appreciated that for some properly fabricated workpieces, there is no occlusion or overlap of features, and thus the methods of the '682 patent cannot even be programmed in learn mode, due to the absence of interfering or occluding elements in the region of interest of a "current feature" on a properly fabricated representative workpiece. Thus, the features associated with the present invention are more general, easier to implement, and yet more robust for certain types of applications, in comparison to the prior art. In particular, the features disclosed herein allow programming in learn mode on a representative workpiece, whether properly fabricated or improperly fabricated, and will still operate reliably in the resulting automatic part program on a run mode workpiece that is either properly fabricated or improperly fabricated.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 3A and 3B show top views of features on a representative workpiece illustrating a current region of interest and edge detection for a current feature for a case of ideal fabrication where a first feature is approximately concentric with the current feature;

FIG. 3C shows a top view of features on a representative workpiece illustrating a region of interest and improper edge detection for a current feature for a case of non-ideal fabrication where an edge of a first feature overlaps with an edge of the current feature;

FIG. 4A shows a top view of the features of FIG. 3C, illustrating a region of interest and edge detection used for characterizing the first feature in order to provide a previously characterized feature;

FIG. 4B shows a top view of the features of FIGS. 3C and 4A illustrating one embodiment of an excluded region based on the previously characterized first feature; and FIG. 4C shows a top view of the features of FIGS. 3C and 4A illustrating a region of interest for the current feature and proper edge detection based on the excluded region of FIG. 4B, for a case of non-ideal fabrication where an edge of the first feature overlaps with an edge of the current feature;

DETAILED DESCRIPTION OF THE PREFERRED EMBODIMENTS

Figure 1:
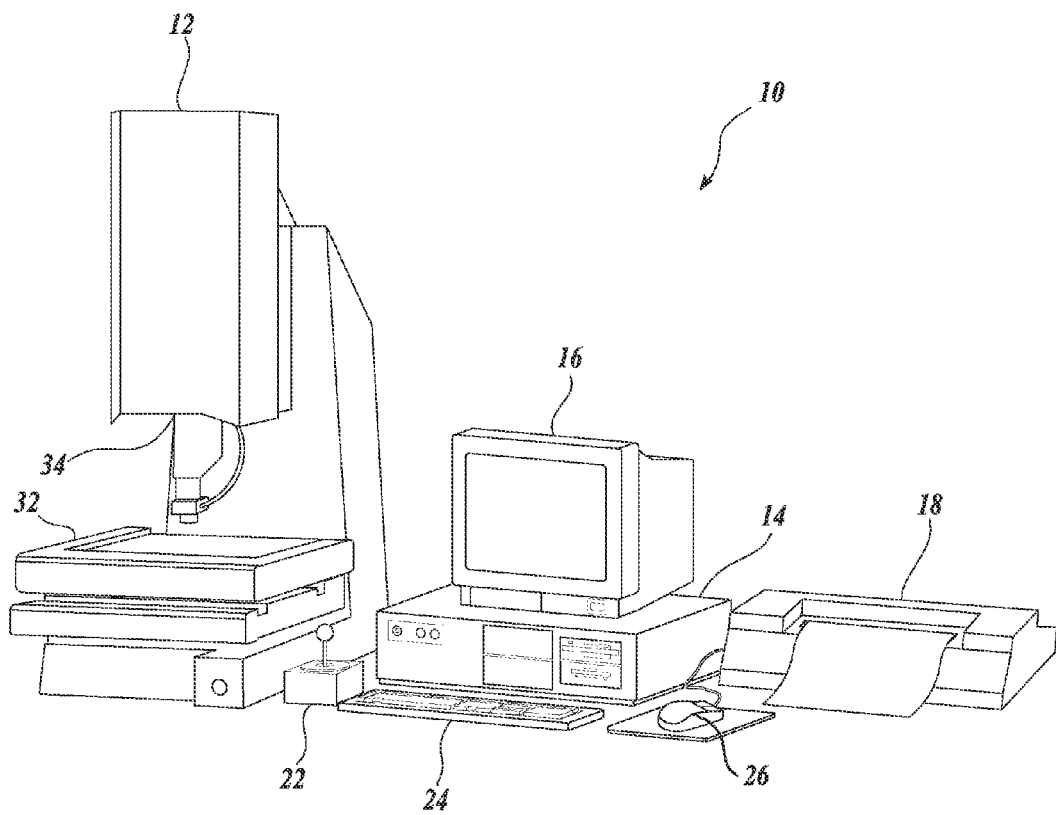
FIG. 1 is a diagram showing various typical components of a general purpose precision machine vision inspection system.

FIG. 1 is a block diagram of one exemplary machine vision inspection system 10 usable in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053, and 7,324,682, and U.S. patent application Ser. Nos. 12/343,383, filed Dec. 23, 2008, and 12/608,943, filed Oct. 29, 2009, which are each incorporated herein by reference in their entireties.

Figure 2:
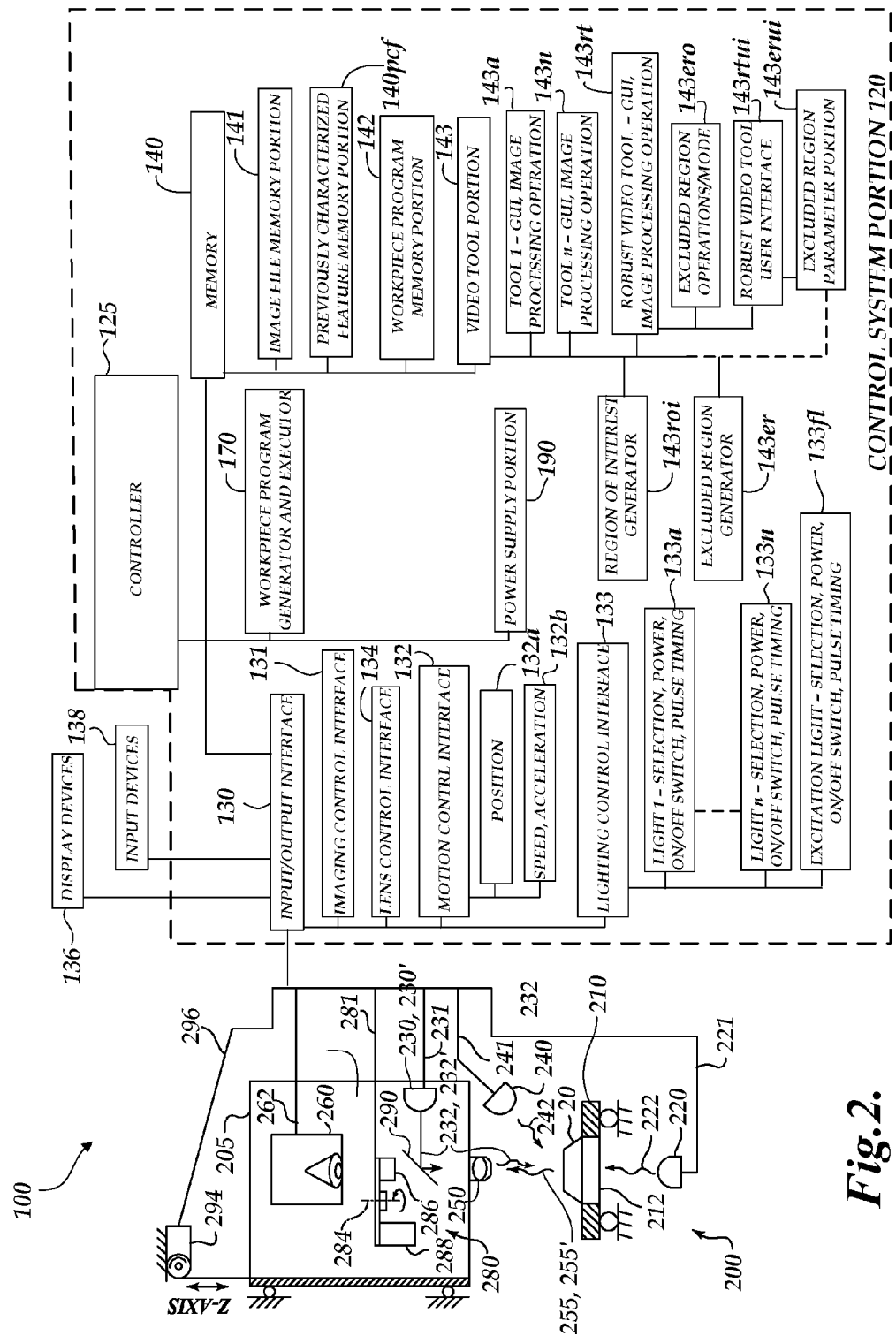
FIG. 2 is a block diagram of a control system portion and a vision components portion of the machine vision inspection system of FIG. 1, and including features according to this invention.

FIG. 2 is a block diagram of a control system portion 120 and a vision components portion 200 of a machine vision inspection system 100 similar to the machine vision inspection system of FIG. 1, and including features according to this invention. As will be described in more detail below, the control system portion 120 is utilized to control the vision components portion 200. The vision components portion 200 includes an optical assembly portion 205, light sources 220, 230, 230', and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included.

The optical assembly portion 205 is controllably movable along a Z-axis that is generally orthogonal to the X and Y axes, by using a controllable motor 294 that drives an actuator to move the optical assembly portion 205 along the Z-axis to change the focus of the image of the workpiece 20. The controllable motor 294 is connected to the input/output interface 130 via a signal line 296.

A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a first coaxial light 230, a second coaxial light 230', and a surface light 240 (e.g., a ring light) may emit source light 222, 232, 232' and/or 242, respectively, to illuminate the workpiece or workpieces 20. The light sources 230 and 230' may emit light 232 and 232' along a path including a minor 290, as described in greater detail below. The second coaxial light 230' may emit source light 232' which has a wavelength profile which causes certain workpiece materials (e.g., solder resist) to fluoresce. Such elements are described in more detail in copending and commonly assigned U.S. patent application Ser. No. 12/904,013, incorporated herein by reference. It will be appreciated that the specific features and elements outlined above for the optical paths providing the source light for fluorescent and non-fluorescent imaging are exemplary only and not limiting. The source light is reflected or transmitted as workpiece light 255, or fluorescent workpiece light 255' is emitted, and the workpiece light used for imaging passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, 230', and 240 may be connected to the control system portion 120 through signal lines or busses 221, 231, and 241, respectively. To alter the image magnification, the control system portion 120 may rotate the turret lens assembly 280 along axis 284 to select a turret lens, through a signal line or bus 281.

As shown in FIG. 2, in various exemplary embodiments, the control system portion 120 includes a controller 125, the input/output interface 130, a memory 140, a workpiece program generator and executor 170, and a power supply portion

190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a, and a speed/acceleration control element 132b, although such elements may be merged and/or indistinguishable. The lighting control interface 133 includes lighting control elements 133a-133n, and 133fl which control, for example, the selection, power, on/off switch, and strobe pulse timing, if applicable, for the various corresponding light sources of the machine vision inspection system 100. The lighting control element 133fl may control the selection, power, on/off switch, and strobe pulse timing, if applicable, for the second coaxial light 230' which may excite fluorescent workpiece materials to emit fluorescent image light.

The memory 140 may include an image file memory portion 141, a previously characterized feature memory portion 140pcf for recording data related to previously characterized features as outlined further below, a workpiece program memory portion 142 that may include one or more part programs, or the like, and a video tool portion 143. The video tool portion 143 includes video tool portion 143a and other video tool portions (e.g., 143n), which determine the GUI, image processing operation, etc., for each of the corresponding video tools, and a region of interest generator 143roi that supports automatic, semi-automatic and/or manual operations that define various ROIs that are operable in various video tools included in the video tool portion 143.

In the context of this disclosure, and as known by one of ordinary skill in the art, the term video tool generally refers to a relatively complex set of operations that a machine vision user can implement through a relatively simple user interface (e.g., a graphical user interface, editable parameter windows, menus, and the like), without creating the step-by-step sequence of operations included in the video tool or resorting to a generalized text-based programming language, or the like. For example, a video tool may include a complex preprogrammed set of image processing operations and computations which are applied and customized in a particular instance by adjusting a few variables or parameters that govern the operations and computations. In addition to the underlying operations and computations, the video tool comprises the user interface that allows the user to adjust those parameters for a particular instance of the video tool. For example, many machine vision video tools allow a user to configure a graphical region of interest indicator through simple "handle dragging" operations using a mouse, in order to define the location parameters of a subset of an image that is to be analyzed by the image processing operations of a particular instance of a video tool. Furthermore, by operating an instance of a video tool during learn mode, with a particular feature of a representative workpiece located in the region of interest, the image processing operations of the video tool may automatically extract certain representative parameters (e.g., the intensity change across an edge feature in the region of interest) that can be saved or recorded in a part program and used as limits to ensure speed or reliability when that instance of the tool (that is, its operations) is automatically run on a corresponding feature on a corresponding workpiece (e.g., an identical part or product) during run mode. This aspect of learn mode operation is referred to as "training" a particular instance of the video tool. It should be noted that the visible user interface features are sometimes referred to as the video tool, with the underlying operations being included implicitly.

It should be appreciated that in contrast to prior art methods, the features and methods disclosed herein related to "excluded region operations" may be implemented using relatively simple video tools that are also useful for operations other than the excluded region operations. Furthermore, the features and methods disclosed herein are robust with respect to the relevant feature relationships (that is, potentially interfering or non-interfering features) both during learn mode and during run mode, despite the fact that they may be implemented by relatively unskilled users.

In particular, the foregoing attributes may be associated with a robust video tool 143rt and an associated excluded region generator 143er, included in the video tool portion 143. Although they are described as separate elements here, in some embodiments the features and operations of the excluded region generator 143er and the robust video tool 143rt may be merged and/or indistinguishable. Briefly, the robust video tool 143rt includes excluded region operations 143ero that prevent a potentially interfering feature from being "confused" with a feature that is intended to be inspected by an instance of the robust video tool 143er. In some embodiments, the robust video tool 143rt may be operated in a mode that includes the excluded region operations 143ero, and at a different time operated in a mode that omits these operations. The robust video tool 143rt also includes a robust video tool interface 143rtui (a user interface), which may include an excluded region parameter portion 143erui. However, in some embodiments, the excluded region parameter portion 143erui may be implemented outside of the robust video tool interface 143rtui (e.g., as a separate interface element, or associated with the excluded region generator 143er). Features and operations associated with these elements are described in greater detail below.

In general, the memory portion 140 stores data usable to operate the vision system components portion 200 to capture or acquire an image of the workpiece 20 such that the acquired image of the workpiece 20 has desired image characteristics. The memory portion 140 may also contain data defining a graphical user interface operable through the input/output interface 130. The memory portion 140 may also store inspection result data, may further store data usable to operate the machine vision inspection system 100 to perform various inspection and measurement operations on the acquired images (e.g., implemented, in part, as video tools), either manually or automatically, and to output the results through the input/output interface 130. As disclosed herein, the memory portion 140 includes a previously characterized feature memory portion 140pcf, which stores data related to certain "previously characterized features" (e.g., features analyzed and characterized using video tools), such that the data may be used by the excluded region generator 143er to determine an excluded region for one or more instances of the robust video tool 143rt. In various embodiments, the previously characterized features may be labeled (e.g., named or numbered) for reference in a user interface. A previously characterized feature may be associated with (or characterized by) a particular measurement result that is stored (e.g., a circle size and location in the case of a circle feature, or a line location and angle in the case of a straight line feature). In some embodiments, a previously characterized feature may also be associated with (or characterized by) the detected edge points that are used to determine its measurement result, and/or statistics or dimensions related to their scatter, or the like, which may be stored. However, in some embodiments, once a previously characterized feature is characterized by a measurement result and/or uncertainty statistics or dimensions, the underlying edge point locations are deleted from memory.

The signal lines or busses 221, 231, and 241 of the stage light 220, the coaxial lights 230 and 230', and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200.

In various exemplary embodiments, when a user utilizes the machine vision inspection system 100 to create a part program for the workpiece 20, the user generates part program instructions either by explicitly coding the instructions automatically, semi-automatically, or manually, using a workpiece programming language, and/or by generating the instructions by operating the machine vision inspection system 100 in a learn mode to provide a desired image acquisition training sequence. For example, a training sequence may comprise positioning a particular workpiece feature of a representative workpiece in the field of view (FOV), setting light levels, focusing or autofocusing, acquiring an image, and providing an inspection training sequence applied to the image (e.g., using an instance of one of the video tools on that workpiece feature). The learn mode operates such that the sequence(s) are captured or recorded and converted to corresponding part program instructions. These instructions, when the part program is executed, will cause the machine vision inspection system to reproduce the trained image acquisition and inspection operations to automatically inspect that particular workpiece feature (that is the corresponding feature in the corresponding location) on a run mode workpiece or workpieces which matches the representative workpiece used when creating the part program.

These analysis and inspection methods that are used to inspect features in a workpiece image are typically embodied in the various video tools (e.g., video tools 143a, 143n, etc.) included in the video tool portion 143 of the memory 140, as outlined above. Many known video tools, or "tools" for short, are included in commercially available machine vision inspection systems, such as the QUICK VISION® series of vision systems and the associated QVPAK® software, discussed above.

It is a particular problem in general purpose machine vision inspection systems to provide methods and tools that allow relatively unskilled users to program such systems with robust inspection operations that reliably provide accurate measurements. The features and operations disclosed herein address this problem in relation to potentially interfering features on a workpiece, such as features that appear on multiple layers or surfaces of a workpiece.

FIGS. 3A and 3B show views 300A and 300B of an image 305 including two features on a representative workpiece, a current feature 320E (which is also a circular edge feature 320E of the region 320) and a potentially interfering feature 310E (which is also a circular edge feature 310E of the region 310). FIGS. 3A-3C also illustrate a current region of interest (as indicated by the ROI indicator 420roi) of a video tool 420 (implied), which is a circle tool used for edge detection of the current feature 320E. Views 300A and 300B illustrate a case of ideal fabrication where the feature 310E is approximately concentric with the current feature 320E. In the examples shown in FIGS. 3A-3C and 4A-4C, the image 305 includes the region 330 (illustrated with a dotted fill pattern) which provides a first intensity (e.g., a region comprising a PCB material covered by a solder resist layer), the region 320 (illustrated with a crosshatched fill pattern) which provides a second intensity (e.g., a region comprising a copper pad covered by the solder resist layer), and the region 310 (illustrated with a dense fill pattern) which provides a third intensity (e.g., a region comprising the copper pad exposed through a hole in the solder resist layer).

As shown in FIGS. 3A and 3B, the circle tool 420 is provided for determining edge points 420EP of the current feature 320E. Exemplary examples of circle and other video tools are described in more detail in U.S. Pat. Nos. 7,627,162 and 7,769,222, which are hereby incorporated by reference in their entireties. The user interface for the circle tool 420 includes the region of interest indicator 420roi having an inner boundary 420in and an outer boundary 420out, a scan direction indicator 422, a sampling direction indicator 428, and an edge selector 424 which is located by the user to indicate a representative portion of the edge that is to be detected. The scan direction indicator 422 is configured to point in the direction corresponding to the sequence that is to be used for the analysis of pixel intensity that is used for detecting the edge in an image. It is generally advantageous that the scan direction proceeds from the least textured or "noisy" side of an edge or boundary to the more noisy side of the edge. In this way, image noise or texture is less likely to be interpreted as the edge, in that the true edge is encountered first in the analysis sequence. The sampling direction indicator 428 shows the direction that the edge point detection scans proceed around the circle tool 420 (e.g., counter-clockwise sampling direction).

In the case shown in FIGS. 3A and 3B, the inner boundary 420in may be configured by a user during learn mode such that it excludes the ideally concentric edge feature 310E from the region of interest 420roi. In such a case, the circle tool 420 is able to accurately determine the edge points 420EP of the current feature 320E without interference from the edge feature 310E. Known circle tools would operate with the desired result in this case. In contrast, as will be described in more detail below with respect to FIG. 3C, in a non-ideal case where the edge feature 310E overlaps the current feature 320E, known circle tools configured and/or trained and recorded as shown in FIGS. 3A and 3B will fail to provide accurate results.

FIG. 3C shows a view 300C of an image 305' including two features corresponding to those discussed above (but on a different workpiece), a current feature 320E (which is numbered the same as in FIGS. 3A and 3B, since it is in the same location in the images 305 and 305') and a potentially interfering feature 310'E (which has changed location in the image 305'). FIG. 3C also illustrates the current region of interest (as indicated by the ROI indicator 420roi) of the video tool 420, used for edge detection of the current feature 320E. View 300C illustrates a case of non-ideal fabrication where the feature 310'E interferes with the current feature 320E (e.g., when the region 310' is a misplaced hole in a solder resist layer, and is not concentric with a copper pad region 320).

As shown in FIG. 3C, in this case the edge points detected at various scan locations in the region of interest 420roi detect a set of edge points that includes the proper edge points 420EP of the current feature 320E, but that also includes the improper edge points 420EP-X, which are edge points of the misplaced interfering feature 310'E. A circle fit to this set of edge points will not reflect the proper size or location of the current feature 320E (or its associated region 320), and thus will lead to improper inspection results, as is typical of known video tools in this case. Since the location of the interfering feature 310'E is not sufficiently predictable for a range of workpieces, this problem cannot be solved by narrowing the region of interest, or other conventional means. Likewise, known region masking techniques cannot be integrated with conventional video tools by relatively unskilled users to produce the desired result. A solution to this problem is described below.

Briefly, as described in greater detail with reference to FIGS. 4A-4C, the features and operations disclosed herein comprise using a simple video tool to characterize a potentially interfering feature, and then using a new type of robust video tool that uses an excluded region based on the previously characterized potentially interfering feature (e.g., characterized by a size and/or location measurement of its actual geometry), to exclude edge points detected in the region of interest around a current feature that are actually edge points of the previously characterized interfering feature. Thus, only valid edge points of the current feature are ultimately identified by the robust video tool, regardless of the location of the potentially interfering features, as desired.

FIGS. 4A and 4B show views 400A and 400B of the image 305' shown in FIG. 3C, including the feature 320E and the potentially interfering feature 310'E (which are numbered the same as in FIG. 3C, since described here is a new way of analyzing the current feature 320E, given the same image 305'). FIGS. 4A and 4B show operations performed prior to using a robust video tool to analyze the current feature 320E.

In particular, FIG. 4A illustrates a region of interest of a video tool 410 (implied), as indicated by the ROI indicator 410roi of the video tool 410, which is used for edge detection and characterization of the potentially interfering feature 310'E. In one embodiment, the video tool 410 may be one of a plurality of standard video tools included in a machine vision inspection system (e.g., as exemplified by the video tools 143a-143n, previously outlined with reference to FIG. 2). As shown in FIG. 4A, in order to encompass all the potential locations of the potentially interfering feature 310'E, and thereby reliably detect it for all cases (e.g., all workpieces, including the cases 310, and 310", shown in dashed outline), the region of interest 410roi must be very wide. The user may configure the ROI inner boundary 410in and the ROI outer boundary 410out during learn mode, based on experience, or the known tolerances of the feature 310'E, etc.

As shown in FIG. 4A, the wide region of interest of the video tool 410 may encompass the feature 320E as well the potentially interfering feature 310'E, which presents the possibility of the video tool 410 detecting edge points of the feature 320E erroneously, rather than the desired edge points of the feature 310'E. However, a number of known measures may prevent this, including the following:

Firstly, if the scan direction is set from "in to out" (in this example), the first edge detected along the scan direction will tend to be the feature 310'E in many cases, since it is nominally smaller than, and inside of, the feature 320E.

Secondly, the feature 310'E exhibits a larger intensity transition than the feature 320E (in this example), and the amount of this large transition can be determined and a related large transition threshold recorded in the tool 410 during learn mode training. When the tool 410 is executed with this threshold as an acceptance criteria (a known practice) the edge points of the feature 320E will then fail to meet this threshold and will not be detected.

Thirdly, it will be appreciated that the effectiveness of the threshold technique outlined above may be enhanced further by using image exposure wavelengths or illumination angles that increase the intensity transition at the edge feature 310'E and/or decrease the intensity transition at the edge feature 320'E. Thus, in some applications (not all), a first image (e.g., an image exposed using a first set of wavelengths) may be used to detect the potentially interfering feature (e.g., the feature 310'E) and a second image may be used to detect a current edge feature using the robust video tool (e.g., the feature 320). In some applications, the first image may be exposed using a first set of wavelengths, and the second image may be exposed using a second set of wavelengths that is different than the first set of wavelengths (e.g., one of the images may be a fluorescent image). In some applications (e.g., when one of the features is a through hole), the hole may be back lighted in one image (e.g., by a stage light) and the other feature may be lighted from the top in another image.

More generally, a user may choose any of the foregoing techniques, and/or choose to measure the larger feature rather than the smaller feature as the previously characterized feature if it exhibits a stronger edge, or the like, in order to provide a reliably characterized previously characterized feature. In the case that a larger feature such as a large circle is used as the previously characterized feature, then it may be the area outside the circle that is the excluded region. Whether it is the area inside or outside a closed form, or the area to the lighter or darker side of a line, that is determined to be the excluded region may be governed by an excluded region polarity parameter that is governed by a default setting, or an algorithm in the excluded region generator, or a setting entered by a user.

As shown in FIG. 4A, using appropriate techniques, the video tool 410 detects the proper edge points 410EP of the potentially interfering feature 310'E at various scan locations in the region of interest 410roi, regardless of its actual location in the region of interest indicated by the ROI indicator 410roi. The video tool 410 may then fit a circle to the set of edge points of the circular edge feature, and characterize related dimensional parameters such as the size and location of the potentially interfering feature 310'E, in order to provide a previously characterized feature that is suitable for determining an excluded region for use with a robust video tool, as described in greater detail below.

FIG. 4B shows a top view 400B of the image 305' illustrating one embodiment of an excluded region based on the previously characterized feature 310'E. The excluded region is indicated by an excluded region indicator ERI. In various embodiments, the excluded region may be determined by an excluded region generator (e.g., the excluded region generator 143er outlined with reference to FIG. 2) based on a set of excluded region parameters defined during learn mode operations. In various embodiments, the set of excluded region parameters includes an identification of a previously characterized feature that is used to determine the excluded region along with other excluded region parameters (e.g., as outlined below with reference to FIG. 5). In the illustrated embodiment, the excluded region is determined based on the previously characterized feature 310'E, such that it encompasses all of the detected edge points 410EP (at least all of the detected edge points that are not outliers). In that case, it is most likely that if any edge point of the interfering edge feature 310'E (the previously characterized feature) would be erroneously detected by a robust video, it will ultimately be excluded (e.g., as outlined below). However, in other embodiments an approach may be taken where the edge points detected by a robust video tool are each "expanded" (e.g., by a dilation around their locations) such that in their expanded form they will partially fall inside an excluded region that does not initially encompass their raw locations. Thus, in various embodiments an excluded region may be generated with various sizes approximating (somewhat larger or less than) that of the previously characterized feature, and reliable excluded region operations may still be performed by a robust video tool as disclosed herein.

For example, in some embodiments, a previously characterized feature may be characterized by a video tool analyzing a workpiece image, detecting edge points of the feature, and fitting a geometric feature to the detected edge points (e.g., a circle) and characterizing the fitted geometric feature with dimensional parameters describing its size and/or location (e.g., a circle center location and radius, or a straight line location and angle). The characterization may be stored in the previously characterized feature memory portion 140*pcf*, outlined with reference to FIG. 2. In some embodiments, the excluded region is determined (e.g., by the excluded region generator 143*er* outlined with reference to FIG. 2) by using the fitted geometric feature as its boundary, or adjusting at least one of the size and the location of the fitted geometric feature (e.g., based on additional parameters in a set of excluded region parameters, as outlined below with reference to FIG. 5) and using that adjusted fitted geometric feature as a boundary of the excluded region, wherein the adjusted fitted geometric feature provides a boundary that encompasses a majority of the detected edge points used for fitting the geometric feature, or the like.

In one embodiment, a circle tool may provide a circularity dimension related to the scatter of the edge points that a circle is fit to for purposes of characterization and the circle may be adjusted based on the circularity dimension. In other embodiments, the excluded region is determined by forming its boundary along line or curve segments joining the detected edge points, or the like. In some embodiments, the adjustment of the size of the excluded region is based on the scan direction (e.g., as indicated by a scan direction indicator or related parameter of the robust video tool), such that the excluded region boundary moves in a direction opposite to that of the scan direction. In some embodiments, this ensures that the scan can "stop" at the excluded region, before detecting any erroneous edge points of a previously characterized interfering feature. However, such methods of determining the excluded region are exemplary only, not limiting. Various other ways of determining an excluded region based on a previously characterized feature may be devised by one skilled in the art based on the teachings of this disclosure. The excluded region may be determined by the excluded region generator 143*er* outlined with reference to FIG. 2, using the characterization stored in the previously characterized feature memory portion 140*pcf*.

FIG. 4C shows a top view 400C of the image 305' illustrating one embodiment of a robust video tool 420' (which may be similar to the video tool 420, except for the addition of elements related to excluded region operations disclosed herein), and illustrating the excluded region discussed in relation to FIG. 4B, as indicated by the excluded region indicator ERI. The robust video tool 420' may be configured similarly or identically to the video tool 420 of FIG. 3C (e.g., the elements 420*roi* and 420'*roi* may be similarly configured, and the elements 422, 428 and 424 may be identical, etc.) However, the robust video tool 420' includes excluded region operations that analyze a workpiece image and determine a set of current-feature edge points 420EP' such that the set of current-feature edge points includes edge points detected in the region of interest 420'*roi* but excludes edge points in the excluded region (indicated by the excluded region indicator ERI). Thus, the robust video tool 420' detects a set of current-feature edge points in the region of interest 420'*roi* that includes the proper edge points 420EP' of the current feature 320E, but excludes (does not include) the improper edge points 420EP-X (shown in FIG. 3C) of the previously characterized feature 310'E which are located in the excluded region (indicated by the indicator ERI) that is determined based on the previously characterized feature 310'E. This desired result is thus achieved in a simple and robust way, regardless of the potentially interfering position of the previously characterized feature 310'E.

In one embodiment, the excluded region operations of the robust video tool 420' that prevent the set of current feature edge points from including edge points located within the excluded region may comprise analyzing the region of interest 420'*roi* to identify a set of "temporary" edge points therein (e.g., all detected edge points therein), then eliminating temporary edge points that are located in the excluded region, and using the remaining temporary edge points as the final set of detected current feature edge points. In another embodiment, the excluded region operations may comprise excluding the excluded region from the region of interest 420'*roi* to form a modified operational region of interest, and analyzing the modified operational region of interest to determine the detected set of current feature edge points.

Figure 5:
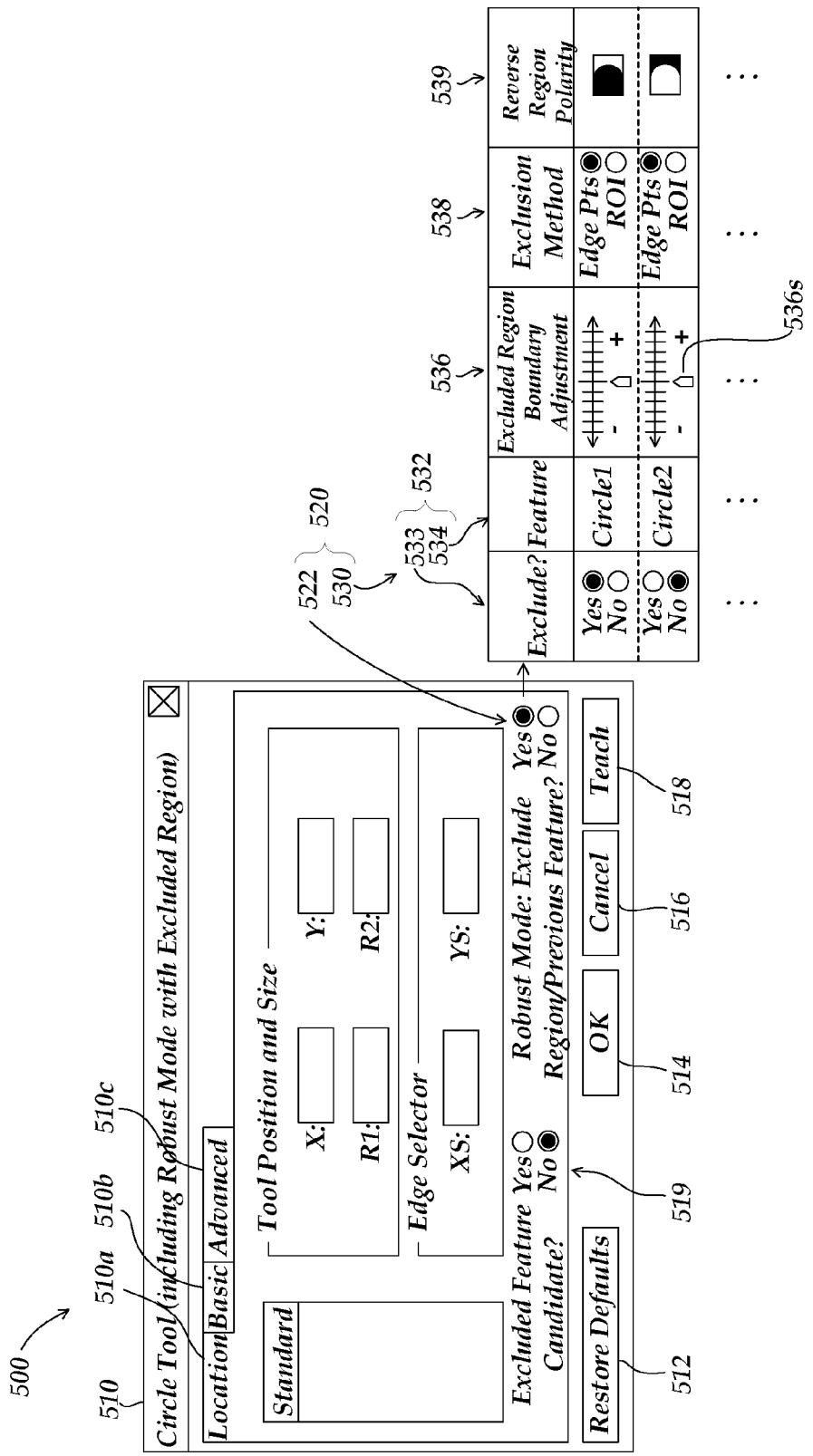
FIG. 5 is a diagram illustrating various features of one embodiment of a robust video tool user interface, including an excluded region parameter portion.

FIG. 5 is a diagram illustrating various features of one embodiment of a robust video tool interface 500 (a user interface), which is displayed and used during learn mode operations in order to define a set of excluded region parameters, including identification of at least one previously characterized feature that is used to determine an excluded region according to the principles disclosed herein. In this example, the robust video tool interface 500 is for a circle-type tool and includes a circle tool parameter dialog box 510 and an excluded region parameter portion 520. The circle tool parameter dialog box 510 includes user-selectable tabbed portions 510*a*, 510*b*, and 510*c*. Similar tabbed portions and features of a video tool are described in more detail in U.S. Pat. No. 7,769,222, which is hereby incorporated by reference in its entirety. For all of the tabbed portions 510*a*-510*c*, the Restore Defaults button 512 at the bottom restores the entries on the tabbed portions 510*b* and 510*c* to their default values, the OK button 514 accepts the current parameters and closes the circle tool parameter dialog box 510, the Cancel button 516 returns all parameters to their state before the current editing sequence began and closes the dialog box 510, and the Teach button 518 executes certain learn mode operations of the tool and trains certain tool parameters based on the current feature (that is, the edge feature in the region of interest) of the representative workpiece used for learn mode.

The tabbed portion 510*a* may reflect the X and Y coordinates of the center of the circle tool ROI, and the inner and outer radii of the circle tool ROI, denoted R1 and R2 respectively. These values may be determined by graphical definition using the region of interest indicator, and/or they may be entered directly in the dialog box. The tabbed portion 510*a* may also reflect the coordinates XS and YS of the edge selector.

As described in more detail in the previously incorporated '222 patent, in certain embodiments the tabbed portion 510*b* may reflect the edge search parameters to be employed within the selected ROI. The tabbed portion 510b may reflect a slope parameter type that specifies whether the edge intensity profile is to exhibit a falling slope (light to dark), a rising slope (dark to light) or any (either) slope when proceeding along the circle edge detection scan line direction indicated by the circle tool. The tabbed portion 510b may reflect a parameter type that specifies whether the edge intensity profile corresponds to a strong edge or a weak edge. Strong edge search criteria may be more stringent to ensure higher reliability in the resulting detection. Conversely, weak edge search criteria sacrifice some reliability, in order to make it more likely that the weak edge will be identified. The tabbed portion 510b may also reflect scan parameters that are used for identifying points along the circle edge in the ROI. Outlier removal may cause geometrically deviant points to be rejected, a scan interval value may cause points to be identified at a spacing of 1 degree, or 5 degrees, etc., and a clockwise or counterclockwise sampling direction may be specified for proceeding with the edge scans.

As also described in more detail in the '222 patent, in certain embodiments the tabbed portion 510c may include a portion that allows selection of a type of filter that may be applied to the image data in the ROI before performing edge detection. In one specific example embodiment, the user may be allowed to select one of four filter types or no filter at all. The user may select a median, an averaging, a Gaussian or a morphology filter. The tabbed portion 510c may also include a portion that reflects edge detection threshold values that may govern edge detection operations. Certain embodiments allow selection of either a static or a dynamic edge threshold. In one specific example embodiment, the user may specify three values TH, THR, and THS. The static threshold value TH defines the mean pixel intensity of the pixels that define an edge. The dynamic threshold value THR modifies the value THS at run time. The edge strength threshold value THS defines the minimum acceptance threshold for the difference in gray scale intensity of the pixels that define the edge of the surface. These thresholds determine whether an edge point is identified along an edge intensity scan line, or whether a scan "fails."

In the embodiment shown in FIG. 5, the robust video tool interface 500 corresponds to a circle-type video tool which may be operated in either the robust "excluded region mode" (that is, a mode which utilizes excluded region operations as disclosed herein), or in a known standard mode (that is, a non-excluded region mode wherein a workpiece image is analyzed and a set of edge points are determined for a current feature in the region of interest without consideration of an excluded region). In this embodiment, the tabbed portion 510a includes an excluded region activation element 522 which may comprise part of the excluded region parameter portion 520, and which is operable by a user to determine whether or not a current instance of the video tool operates in the excluded region mode (e.g., using excluded region operations) or in the non-excluded region mode. In this particular embodiment, the excluded region activation element 522 comprises a pair of "yes/no" radio buttons which toggle based on a user selection. In one embodiment, the excluded region parameter portion 520 only appears on the display when the "yes" radio button is selected (that is, when the robust excluded region mode operations are to be used). It will be appreciated that in other embodiments, these different "modes" may be implemented using two separate circle-type video tools, instead.

In the embodiment shown in FIG. 5, the tabbed portion 510a also includes an excluded feature candidate indicator 519 comprising a pair of "yes/no" radio buttons which toggle based on a user selection in order to determine whether a feature characterized by a current instance of the tool will be included in a list of "excluded feature candidates". For example, when the robust mode is not activated in the video tool interface 500, a user may want to use a current instance of the video tool to characterize a feature in order to provide a previously characterized feature, as disclosed herein. In that case, it may be useful to use the indicator 519 to mark the current feature for inclusion in a candidate list of previously characterized features and/or record certain learned parameters and/or detected edge points that may not otherwise be recorded, for later use by the excluded region generator.

The excluded region parameter portion 520 includes an excluded region parameter dialog box 530 which may be configured to define the members of a current instance of a set of excluded region parameters (e.g., the parameters used by the excluded region generator) used to generate an excluded region corresponding specifically to the current instance of the robust video tool. In the embodiment shown in FIG. 5, the excluded region parameter dialog box 530 includes an identification portion 532, an excluded region boundary adjustment element in column 536, an exclusion method selection element in column 538, and a reverse region polarity selection element in column 539.

The identification portion 532 identifies the previously characterized feature(s) that is(are) used to determine the excluded region. In the illustrated embodiment, the identification portion 532 comprises a column 534 including a list of previously characterized features, and a column 533 including a corresponding list of selection elements, which are configured by the user to provide the identification of which specific previously characterized features in column 534 that will be used to determine the excluded region for the current instance of the robust video tool. In this particular embodiment, each selection element comprises a pair of "yes/no" radio buttons which toggle based on a user selection, to indicate whether the corresponding feature in column 534 is used to determine the excluded region (e.g., whether it is included in the excluded region), or not. In one embodiment, the list of previously characterized features in column 534 is automatically generated by the control system of the machine vision inspection system. In one embodiment, the list may include all previously characterized features. In another embodiment, the list may include all previously characterized features which are also located within the current image. In another embodiment, the list may include all previously characterized features which are proximate to (e.g., within a predetermined distance of) a defined region of interest of a current instance of the robust video tool. In yet other embodiments, the robust video tool operations and/or the excluded region generator may automatically identify the previously characterized feature which is closest to the current instance of the robust video tool (that is, closest to its region of interest) as a previously characterized feature to be included in a current set of excluded region parameters that is used to determine the excluded region for the current instance of the robust video tool. In such an embodiment, the identification portion 532 may be omitted.

Figure 6:
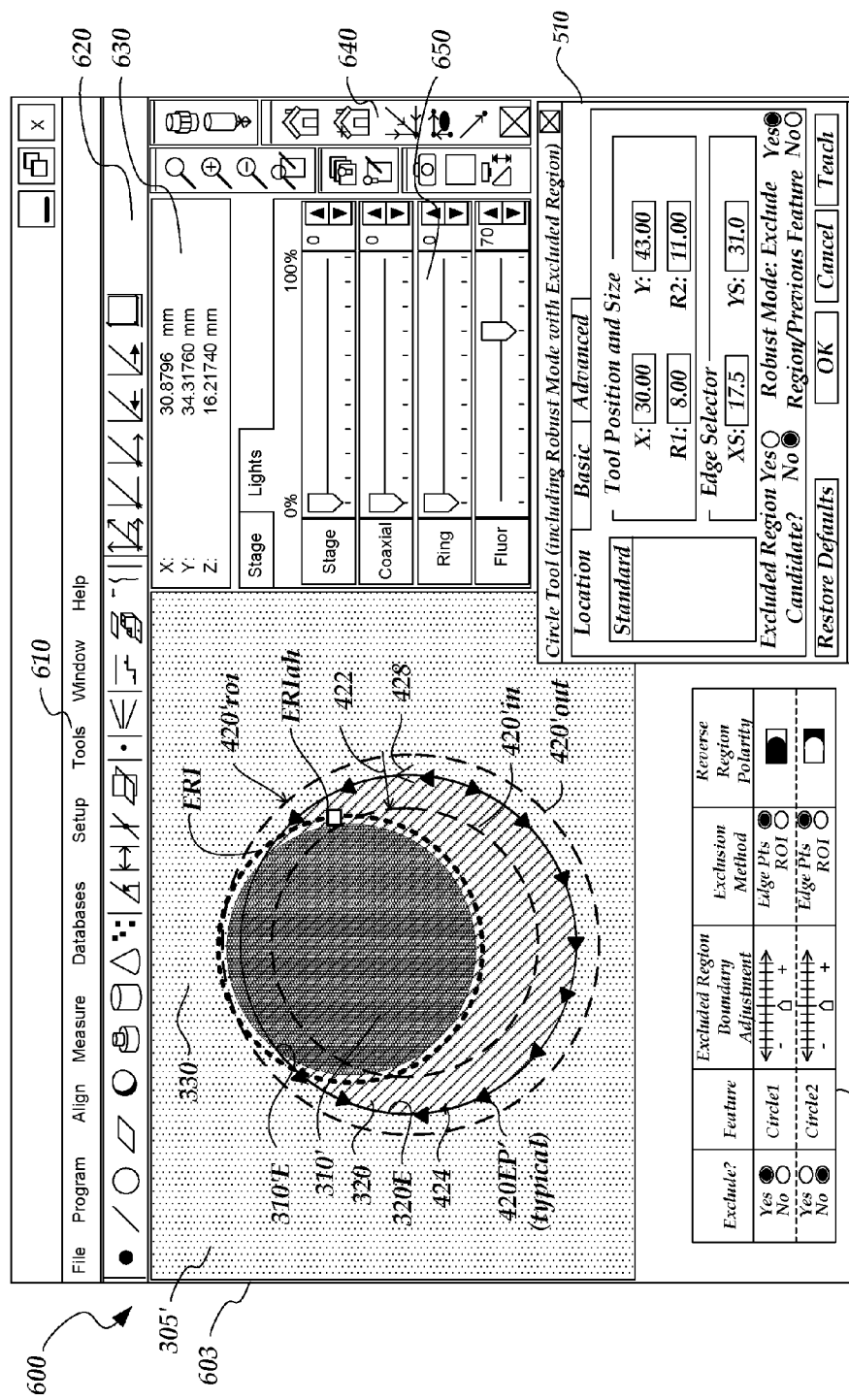
FIG. 6 is a diagram illustrating various features of one embodiment of a user interface during learn mode operations, including a workpiece image, an excluded region parameter portion, a region of interest indicator, and an excluded region indictor.

As previously outlined, the size of the excluded region may be adjusted based on adjusting a dilation of detected edge points, or adjusting the size of a fitted geometric feature, or the like (e.g., such that the excluded region encompasses a majority of the detected edge points of the previously characterized feature). The excluded region boundary adjustment element in column 536 may be set by the user to govern the size of such adjustments. In the embodiment shown in FIG. 5, the excluded region boundary adjustment element in column 536 comprises a slider 536s, which may be dragged by the user to determine the amount of adjustment. However, in other embodiments, the user may enter a number of pixels (or other units) as an adjustment amount. In other embodiments, the user may drag a handle on a displayed excluded region indicator (e.g., as shown in FIG. 6), or the adjustment may be automatic (e.g., based on a default amount, or a determined scatter parameter of the previously characterized feature, or the like), and the excluded region boundary adjustment element in column 536 may be omitted.

As previously outlined, the excluded region operations of the robust video tool that prevent the set of current feature edge points from including edge points located within the excluded region may comprise analyzing the region of interest to identify a set of "temporary" edge points therein, then eliminating temporary edge points that are located in the excluded region, and using the remaining temporary edge points as the final set of detected current feature edge points. In another embodiment, the excluded region operations may comprise excluding the excluded region from the region of interest to form a modified operational region of interest, and analyzing the modified operational region of interest to determine the detected set of current feature edge points. In one embodiment, the exclusion method selection element shown in column 538 may be used by the user to select which of these methods is applied. In other embodiments, the method may be predetermined and the element in column 538 may be omitted.

As previously outlined, a user may choose to measure a larger feature rather than a smaller feature as the previously characterized feature if it exhibits a stronger edge, or the like, in order to provide a reliably characterized previously characterized feature. In the case that a larger feature such as a large circle is used as the previously characterized feature, then it may be the area "outside the circle" that is the excluded region applicable to a current instance of a robust video tool. In one embodiment, the reverse region polarity selection element in column 539, comprising a toggle switch icon that may be clicked by a user to reverse the polarity, may be used by the user to select the "polarity" of an excluded region relative to a previously characterized feature. In other embodiments, the polarity may be automatically determined based on other parameters of the current instance of the robust video tool and/or the relevant previously characterized feature(s), and the element in column 539 may be omitted.

It will be appreciated that the foregoing embodiments of user interface features are exemplary only, and not limiting. Other features usable to enter and/or alter the members of a set of excluded region parameters in the context of a robust video tool user interface will be apparent to one skilled in the art based on this disclosure.

FIG. 6 is a diagram illustrating various features of one embodiment of a user interface display 600 during learn mode operations. In the exemplary state shown in FIG. 6, the user interface display 600 includes a field of view window 603 that displays a workpiece image 305', and several numbered elements and features of a robust video tool interface, as previously described with reference to FIG. 4C, such as the elements 420'roi, 420'in, 420'out, 422, 424, 428, and ERI, for example, as well as the robust video tool interface elements 510 and 530, previously described with reference to FIG. 5. The user interface display 600 also includes various measurement and/or operation selection bars such as the selection bars 620 and 640, a real-time X-Y-Z (position) coordinate window 630, and a light control window 650.

In various embodiments, the user may create a current instance of a robust video tool by selecting a robust video tool from a drop down menu or toolbar that displays a plurality of alternative video tools and/or mode selection buttons, all accessed under the tools menu element 610. Upon such a selection, in one embodiment, the user interface may automatically display the region of interest indicator 420'roi in a default position, as well as the previously described robust circle tool parameter dialog box 510 and the excluded region parameter dialog box 530, for configuring the various parameters of the selected robust video tool, as outlined above.

In various embodiments, the robust video tool interface displays the region of interest indicator 420'roi and the excluded region indicator ERI of the robust video tool superimposed upon the current feature 320E to be inspected, as shown in the field of view window 603. In various embodiments, the excluded region indicator ERI may appear automatically, as determined based on the closest previously characterized feature to the current region of interest 420'roi, or as soon as a previously characterized feature is selected using the appropriate columns of the excluded region parameter dialog box 530 (as outlined above with reference to FIG. 5), or the like. In the embodiment shown in FIG. 6, the excluded region indicator ERI includes a size adjustment handle ERIah, which may be engaged using a mouse and dragged by the user to resize the excluded region (e.g., as generated by the excluded region generator according to principles outlined above) and define or redefine associated adjustment parameters. In various embodiments, the excluded region indicator ERI may automatically change on the display when changes are made in a current instance of the set of excluded region parameters using the excluded region parameter dialog box 530, or the like.

In the example shown in FIG. 6, the excluded region indicated by the excluded region indicator ERI corresponds to the previously characterized feature "Circle1" selected in the excluded region parameter dialog box 530. As indicated by its name, Circle1 is a previously characterized feature that was characterized by using a circle tool included in the plurality of video tools (e.g., tools accessible using the Tools menu element 610) to detect its edge points and characterize its dimensional parameters, for example. In one embodiment, as outlined above, the excluded region indicator ERI may automatically appear at the previously characterized location of the feature Circle1, as soon as Circle1 is selected using the appropriate columns of the excluded region parameter dialog box 530 (as outlined above with reference to FIG. 5), and the excluded region generator determines the excluded region based on the selected Circle1 and on related parameters defined in the excluded region parameter dialog box 530. In one embodiment, the stored characterization data of the feature Circle1 may correspond to a circle fitted to edge points of the previously characterized edge feature 310'E (e.g., as characterized by a circle tool), and the excluded region indicator ERI may initially correspond to an excluded region determined based on that fitted circle, with a default or user entered amount of adjustment as indicated in the adjustment column of the excluded region parameter dialog box 530. Desirably, the amount of adjustment should be set such that any observable edge points of the previously characterized edge feature 310'E fall within the excluded region, so that the excluded region operations of the robust video tool (e.g., the operations that determine the set of current-feature edge points 420EP' such that the set includes edge points detected in the region of interest 420'roi and does not include edge points located within the excluded region indicated by ERI) do not allow them to be included in the set of current-feature edge points 420EP' of the current feature 320E, which is to be detected and analyzed by the current instance of the robust video tool.

As previously outlined, in various embodiments, the machine vision inspection system (e.g., the system 100, shown in FIG. 2) comprises a learn mode of operation and a run mode of operation. Its user interface is configured to define the parameters of at least one instance of a video tool included in a plurality of video tools (e.g., the video tools 143a-143n shown in FIG. 2) in order to provide the at least one previously characterized feature (e.g., the feature Circle1, shown in FIG. 6) using a representative workpiece during the learn mode of operation. The robust video tool interface (e.g., comprising the elements 510, 520, and 530 shown in FIGS. 5 and 6) is configured to define the parameters of a current instance of the robust video tool used to determine a set of current-feature edge points for a current feature (e.g., the set of current-feature edge points 420EP' of the current feature 320E, shown in FIG. 6), on the representative workpiece during the learn mode of operation. The machine vision inspection system is configured to record the parameters defined during the learn mode of operation in a part program, including the defined parameters of the at least one video tool used to provide the at least one previously characterized feature, the defined parameters of the current instance of the robust video tool, and the defined set of excluded region parameters. The machine vision inspection system is also configured to execute operations of the part program during the run mode of operation for a run mode workpiece similar to the representative workpiece, wherein the operations of the part program comprise (a) using the recorded defined parameters of the current instance of the at least one video tool to provide characterization of the at least one previously characterized feature on the run mode workpiece, (b) using the recorded defined excluded region parameters to determine the excluded region based on the at least one previously characterized feature on the run mode workpiece, and (c) using the recorded defined parameters of the current instance of the robust video tool to determine a set of current-feature edge points for the current feature on the run mode workpiece such that the set of current-feature edge points includes edge points detected in the region of interest of the current instance of the robust video tool on the run mode workpiece and does not include edge points located within the excluded region that is determined based on the at least one previously characterized feature on the run mode workpiece.

As previously indicated, the features of the present invention are more general, easier to implement, and yet more robust for certain types of applications, in comparison to the prior art. In particular, the operations and features disclosed above are video tool operations and features operable by a relatively unskilled user. Importantly, the disclosed features and operations allow programming in learn mode on a representative workpiece that is either properly fabricated or improperly fabricated, and will still operate reliably in the resulting automatic part program on a run mode workpiece that is either properly fabricated or improperly fabricated.

It should be appreciated that although the examples illustrated and discussed herein use previously characterized and current features which are circle features characterized using circle-type video tools, that similar teachings and principles may be implemented using other types of video tools, such as arc tools which use an arc shaped region of interest, or tools that characterize a straight edge and use a rectangular region of interest, or the like. Such tools are known in the art, and may be modified to add the features of a robust video tool according to this invention, based on the teachings and principles disclosed herein.

Furthermore, although the examples illustrated and discussed herein use excluded regions which are defined to correspond to a specific instance of a robust video tool, the principles disclosed herein may also be applied and/or implemented globally. For example, in one embodiment, a set of one or more robust video tools may be defined during learn mode, wherein each tool comprises the excluded region operations outlined above. A set of previously characterized features that are used to determine the excluded region may also be defined during learn mode (e.g., in one embodiment, by implementing an element analogous to the element 519 shown in FIG. 5, in various video tools). In one embodiment, a dialog box similar to the excluded region parameter dialog box 530 may be used to define related excluded region parameters for each member or all of the set of previously characterized features. Then, at the end of learn mode, or another appropriate time, the excluded region generator may generate a "global" excluded region which comprises a set of excluded regions corresponding to that defined set of previously characterized features. Then each robust video tool may refer to the global excluded region when performing its excluded region operations.

While various exemplary embodiments of the present invention have been illustrated and described, numerous variations in the illustrated and described arrangements of features and sequences of operations will be apparent to one skilled in the art based on this disclosure. In other embodiments, new types of video tools specific to utilizing the excluded region methods of the present invention may be provided. Other video tool embodiments and associated graphical user interface features will be apparent to one of ordinary skill in the art having the benefit of the general teachings disclosed herein. Thus, it will be appreciated that various changes according to the teachings herein can be made to the various particular embodiments outlined above without departing from the spirit and scope of the invention.

The embodiments of the invention in which an exclusive property or privilege is claimed are defined as follows:

1. A machine vision inspection system operable to inspect potentially interfering features on a workpiece, the machine vision inspection system comprising:
   a control system comprising a memory element and an excluded region generator;
   an imaging system operable to provide workpiece images;
   a display usable to display workpiece images and user interface elements;
   a user interface usable to define a sequence of workpiece inspection operations including video tool operations which analyze workpiece images, detect edge points of a workpiece feature, and characterize at least the location of the workpiece feature; and
   a plurality of video tools including a robust video tool that performs edge detection, the robust video tool comprising:
      a region of interest;
      a robust video tool interface included in the user interface;
      operations that detect edge points in the region of interest; and
      excluded region operations that analyze a workpiece image and determine a set of current-feature edge points such that the set of current-feature edge points includes edge points detected in the region of interest and does not include edge points located within an excluded region that is determined based on at least one previously characterized feature, wherein:
the at least one previously characterized feature is a feature characterized by using one of the plurality of video tools to analyze a workpiece image to detect edge points of the previously characterized feature and characterize a dimensional parameter of the previously characterized feature based on the detected edge points, and
the excluded region generator is configured to determine the excluded region based on the at least one previously characterized feature.

2. The machine vision inspection system of claim 1, wherein the excluded region generator is configured to determine the excluded region based on a set of excluded region parameters defined during a learn mode of operation of the machine vision inspection system, the set of excluded region parameters including an identification of the at least one previously characterized feature that is used to determine the excluded region.

3. The machine vision inspection system of claim 2, wherein:
the machine vision inspection system comprises the learn mode of operation and a run mode of operation;
the user interface is configured to define the parameters of at least one instance of a video tool included in the plurality of video tools in order to provide the at least one previously characterized feature using a representative workpiece during the learn mode of operation;
the robust video tool interface is configured to define the parameters of a current instance of the robust video tool used to determine a set of current-feature edge points for a current feature on the representative workpiece during the learn mode of operation;
the machine vision inspection system is configured to record the parameters defined during the learn mode of operation in a part program, including the defined parameters of the at least one video tool used to provide the at least one previously characterized feature, the defined parameters of the current instance of the robust video tool, and the defined set of excluded region parameters; and
the machine vision inspection system is configured to execute operations of the part program during the run mode of operation for a run mode workpiece similar to the representative workpiece, wherein the operations of the part program comprise:
using the recorded defined parameters of the current instance of the at least one video tool to provide characterization of the at least one previously characterized feature on the run mode workpiece;
using the recorded defined excluded region parameters to determine the excluded region based on the at least one previously characterized feature on the run mode workpiece; and
using the recorded defined parameters of the current instance of the robust video tool to determine a set of current-feature edge points for the current feature on the run mode workpiece such that the set of current-feature edge points includes edge points detected in the region of interest of the current instance of the robust video tool on the run mode workpiece and does not include edge points located within the excluded region that is determined based on the at least one previously characterized feature on the run mode workpiece.

4. The machine vision inspection system of claim 3, wherein:
the user interface is configured to display an image of the representative workpiece during the learn mode of operation;
the user interface is configured such that a user can select and configure the at least one instance of a video tool included in the plurality of video tools, wherein that video tool is one of a circle tool having an annular region of interest, an arc tool having an arc-shaped region of interest, and a tool that characterizes a straight edge and has a rectangular region of interest, and a user interface of that video tool includes a region of interest indicator which is superimposed on the displayed image of the representative workpiece, and the user interface of that video tool is configured by the user in order to define the parameters of an instance of that video tool in order to provide the at least one previously characterized feature using the representative workpiece during the learn mode of operation; and
the user interface is configured such that a user can select and configure an instance of the robust video tool, wherein the robust video tool is one of a circle tool having an annular region of interest, an arc tool having an arc-shaped region of interest, and a tool that characterizes a straight edge and has a rectangular region of interest, and the robust video tool interface includes a region of interest indicator and an excluded region indicator which are superimposed on a displayed image of the representative workpiece, and the robust video tool interface is configured by the user in order to define the parameters of the current instance of the robust video tool used to determine the set of current-feature edge points for a current feature on the representative workpiece during the learn mode of operation.

5. The machine vision inspection system of claim 2, wherein the excluded region generator is configured to automatically identify a previously characterized feature that is closest to a current instance of the robust video tool used to determine a set of current-feature edge points for a current feature on the representative workpiece during the learn mode of operation, and to automatically include an identification of that previously characterized feature in the set of excluded region parameters that is used to determine the excluded region.

6. The machine vision inspection system of claim 2, wherein:
the user interface comprises an excluded region parameter portion which is configured to define members of the set of excluded region parameters during the learn mode of operation of the machine vision inspection system; and
the defined members include an identification of the at least one previously characterized feature used to determine the excluded region.

7. The machine vision inspection system of claim 6, wherein the excluded region parameter portion comprises an excluded feature identifier that is configured by the user to provide the identification of the at least one previously characterized feature that is used to determine the excluded region.

8. The machine vision inspection system of claim 7, wherein the excluded region parameter portion comprises a list of previously characterized features that is automatically generated by the control system and the excluded feature identifier comprises a selection element that is configured to select at least one member of the list to include in the identification of the at least one previously characterized feature that is used to determine the excluded region.

9. The machine vision inspection system of claim 6, wherein:
- the robust video tool interface is configured to define the parameters of a current instance of the robust video tool during the learn mode of operation;
- the excluded region parameter portion is included in the robust video tool interface; and
- the excluded region parameter portion is configured to define a current instance of the set of excluded region parameters for an excluded region corresponding specifically to the current instance of the robust video tool, the current instance of the set of excluded region parameters including an identification of a current instance of the at least one previously characterized feature that is used to determine the excluded region.

10. The machine vision inspection system of claim 9, wherein the robust video tool interface comprises a region of interest indicator and an excluded region indicator which are displayed superimposed on an image of the representative workpiece during the learn mode of operation.

11. The machine vision inspection system of claim 10, wherein the region of interest indicator automatically changes when the current instance of the set of excluded region parameters is changed.

12. The machine vision inspection system of claim 10, wherein the excluded region indicator is configured to be altered by user to adjust the size of the excluded region indicator and make a corresponding change in the current instance of the set of excluded region parameters.

13. The machine vision inspection system of claim 2, wherein the excluded region generator is configured to determine the excluded region such that it encompasses at least a majority of the edge points detected while characterizing the at least one previously characterized feature that is used to determine the excluded region.

14. The machine vision inspection system of claim 1, wherein:
- a previously characterized feature is a feature characterized by using one of the plurality of video tools to perform operations comprising (a) analyzing a workpiece image to detect edge points of that feature; (b) fitting a geometric feature to the detected edge points; and (c) providing a characterization of the fitted geometric feature, that characterization comprising at least a dimensional parameter of the fitted geometric feature; and
- the excluded region generator is configured to determine the excluded region based on the characterization of the fitted geometric feature of at least one previously characterized feature.

15. The machine vision inspection system of claim 14, wherein;
- the excluded region generator is configured to determine the excluded region by adjusting at least one of the size and the location of the fitted geometric feature and using that adjusted fitted geometric feature as a boundary of the excluded region, wherein the adjusted fitted geometric feature provides a boundary that encompasses at least a majority of the detected edge points used for fitting the geometric feature.

16. The machine vision inspection system of claim 15, wherein the robust video tool comprises a scan direction that is used in its operations that detect edge points in the region of interest, and the excluded region generator is configured to adjust the fitted geometric feature such that the boundary moves in a direction opposite to that scan direction.

17. The machine vision inspection system of claim 14, wherein the previously characterized feature is a feature characterized by using a circle tool included in the plurality of video tools, the fitted geometric feature is a circle, and the robust video tool is a circle tool.

18. The machine vision inspection system of claim 1, wherein the robust video tool comprises:
- an excluded region mode wherein the excluded region operations are performed;
- a non-excluded region mode comprising non-excluded region operations that analyze a workpiece image and determine a set of current-feature edge points such that the set of current-feature edge points includes edge points detected in the region of interest without consideration of an excluded region; and
- the robust video tool interface includes an excluded region activation element which is operable by a user to determine whether or not an instance of the robust video tool operates in the excluded region mode or the non-excluded region mode.

19. The machine vision inspection system of claim 1, wherein:
- the excluded region generator is configured to determine the excluded region based on at least one previously characterized feature that is a feature characterized by using one of the plurality of video tools in a first workpiece image that is exposed using a first set of wavelengths; and
- the robust video tool is configured to detect the set of current feature edge points in a second workpiece image that is exposed using a second set of wavelengths that is different than the first set of wavelengths.

20. The machine vision inspection system of claim 19, wherein one of the first and second sets of wavelengths includes a fluorescent wavelength emitted by the workpiece with a significant intensity, and the other of the first and second sets of wavelengths does not include the fluorescent wavelength emitted by the workpiece with a significant intensity.

* * * * *